(12) United States Patent
Xu et al.

(10) Patent No.: US 9,091,687 B2
(45) Date of Patent: Jul. 28, 2015

(54) ELISPOT DIAGNOSTIC KIT FOR NEUROMYELITIS OPTICA AND ITS APPLICATION

(71) Applicants: Jun Xu, Nanjing (CN); Shuli Zhao, Nanjing (CN); Xinxin Chen, Nanjing (CN); Jianqun Shi, Nanjing (CN); Yinwei Zhu, Nanjing (CN); Yingdong Zhang, Nanjing (CN); Yin Hong, Nanjing (CN)

(72) Inventors: Jun Xu, Nanjing (CN); Shuli Zhao, Nanjing (CN); Xinxin Chen, Nanjing (CN); Jianqun Shi, Nanjing (CN); Yinwei Zhu, Nanjing (CN); Yingdong Zhang, Nanjing (CN); Yin Hong, Nanjing (CN)

(73) Assignee: Jun Xu, Nanjing (CN)

( * ) Notice: Subject to any disclaimer, the term of this patent is extended or adjusted under 35 U.S.C. 154(b) by 0 days.

(21) Appl. No.: 14/123,500

(22) PCT Filed: Apr. 16, 2013

(86) PCT No.: PCT/CN2013/000440
§ 371 (c)(1),
(2) Date: Dec. 3, 2013

(87) PCT Pub. No.: WO2014/067229
PCT Pub. Date: May 8, 2014

(65) Prior Publication Data
US 2015/0140569 A1   May 21, 2015

(30) Foreign Application Priority Data

Oct. 31, 2012   (CN) .......................... 2012 1 0426031

(51) Int. Cl.
G01N 33/53      (2006.01)
G01N 33/543     (2006.01)
C07K 14/47      (2006.01)

(52) U.S. Cl.
CPC .......... *G01N 33/54306* (2013.01); *C07K 14/47* (2013.01); *G01N 2333/47* (2013.01); *G01N 2800/285* (2013.01)

(58) Field of Classification Search
None
See application file for complete search history.

(56) References Cited

U.S. PATENT DOCUMENTS 4,208,479 A * 6/1980 Zuk et al. .................. 435/7.9

OTHER PUBLICATIONS

Jarius et al. (Nat. Rev. Neurol. 2010 vol. 6, p. 383-392).*

* cited by examiner

*Primary Examiner* — Jacob Cheu
(74) *Attorney, Agent, or Firm* — CBM Patent Condulting, LLC

(57) ABSTRACT

An ELISpot diagnosis kit for NMO and its application are characterized in that, the polypeptide fragment specific to NMO effector T-cell is obtained through topological conformation analysis of aquaporin-4 (AQP-4), followed by the structural analyses of the related polypeptides after combination and rearrangement so as to screen out the brand-new polypeptide fragment suitable for NMO disease diagnosis. In the ELISpot experiment, by utilizing the obtained polypeptide fragment, stimulate the effector T-cell in the NMO disease to secrete IL-4, proving the feasibility and scientific value of that polypeptide fragment in the NMO diagnosis. This method is with strong specificity, high sensitivity and easy operations, and it can be developed into the diagnosis kit for the diagnosis and differential diagnosis of NMO in the clinical examination, laying the foundation for the early discovery and treatment of NMO.

4 Claims, 2 Drawing Sheets

SEQUENCE LISTING

```
<160> NUMBER OF SEQ ID NOS: 1

<210> SEQ ID NO 1
<211> LENGTH: 37
<212> TYPE: PRT
<213> ORGANISM: Homo sapiens

<400> SEQUENCE: 1

Ile Met Val Ala Phe Lys Gly Val Trp Thr Gln Ala Phe Trp Lys Cys
1               5                   10                  15

Leu Val Thr Pro Pro Ser Val Val Gly Gly Leu Gly Val Thr Met Val
            20                  25                  30

His Gly Asn Leu Thr
        35
```

ELISPOT DIAGNOSTIC KIT FOR NEUROMYELITIS OPTICA AND ITS APPLICATION

This application is the U.S. national phase of International Application No. PCT/CN2013/000440 Filed on 16 Apr. 2013, which designated the U.S. and claims priority to Chinese Application No. CN201210426031.4 filed on 31 Oct. 2012, the entire contents of each of which are hereby incorporated by reference.

TECHNICAL FIELD

This invention relates to the ELISpot diagnosis kit for neuromyelitis optica and its application, belonging to the technical field of medical immunology diagnosis, particularly to the application of diagnosis of neuromyelitis optica with the ELISpot method.

BACKGROUND OF THE INVENTION

In the existing techniques, the cause of neuromyelitis optica (NMO, also known as the Devic disease) is unclear, with most clinical manifestations of bilateral acute neuritis or retrobulbar optic neuritis as well as paraplegia caused by the myelitis simultaneously or before or after the occurrence of optic neuritis. Victims mostly suffer from acute visual acuity or complete loss of sight, and the eye-ground is shown as optic disc hyperemia and edema (the optic neuritis type) or normal eye-ground (the retrobulbar optic neuritis type). Additionally, there has not yet been with changes like torpor or loss of reflection of pupillary light reflex, huge central scotoma or centripetal narrowing of field of vision, seldom with ophthalmoplegia externa. The mortality of this disease is approximately 50%, mostly as deaths from paralysis of respiratory muscle or secondary infection in the lung or urinary system. However, current detections of this disease mostly rely on clinical diagnosis, and the accuracy rate is significantly affected by the ability of the doctor in charge.

Aquaporin-4 (AQP-4) is a member of aquaporin protein family of mediate water transmembrane transport, concentrated on the astrocytus foot process or ependymal cell surface around the brain blood capillary of central nervous system in the form of polarization. Studies show that AQP-4 extensively exists in subarachnoid space, circumvascular spongiocytes, ependymal cells and osmoreceptor organs, and it may adjust the volume of cerebrospinal fluid and cell sap. Kiening et al discover in studies that, the expression of AQP-4 at 72 hours after cerebral ischemia rises proportionally to cerebral edema, while cerebral edema is significantly alleviated in the model of AQP-4 gene knock-out mouse. The above researches and studies show that, AQP-4 plays a critical role in the adjustment of water metabolism of brain tissue, and it also participates in the outbreak of NMO. Recent studies show that, the AQP-4 autoantibody exists in the blood serum of NMO victims, while it does not exist in the blood serum of multiple sclerosis victims. After the international NMO diagnosis standard has adopted the detection of AQP-4 antibody as a core supporting condition for the diagnosis of NMO since 2006, it has highly important clinical guidance significance to the clinical early confirmed diagnosis of NMO and the differential diagnosis of other demyelinating diseases.

It is discovered in applying 15 polypeptide superimpositions of amino acid for the immunogenicity analysis of AQP-4 protein that, different peptide fragments of AQP-4 have different immunogenicities on the T-cell, among which the 22-36 amino acid inside the N-terminal intracellular domain, the 82-108/211-225/235-249 amino acid in the transmembrane domain, the extracellular 139-153 and the 289-306 amino acid inside the C-terminal intracellular domain have strong T-cell immunogenicity.

The Enzyme-linked Immunospot (ELISpot) technique established in 1983 is with high sensitivity and extensive application, currently as one of the most important detection means for immunodetection of antigenic specificity immunoreaction. This invention constructs the antigen polypeptide with specific effector T cell in combination with the features of AQP-4 antigenic structure, and utilizes the ELISpot method to diagnose the NMO disease.

SUMMARY OF INVENTION

The object of this invention is to, based on the features of human AQP-4 antigen structure, connect the polypeptide fragments with strong immunogenicity (23-36 and 135-155 amino acids) into a brand new amino acid sequence, forming the ELISpot diagnosis kit, for detecting the specific IL-4 T-cells secreted in the peripheral blood of NMO victims, improving the sensitivity and specificity of NMO detection and assisting with the diagnosis and differential diagnosis of NMO.

The technical solution of this invention is: a polypeptide fragment suitable for the diagnosis of NMO with the ELISpot method, and its amino acid sequence is as follows: IMVAFKGVWTQAFWKCLVTPPSVVG-GLGVTMVHGNLT (SEQ ID NO: 1).

Another object of this invention is to provide a kit for ELISpot diagnosis of NMO, which consists of the ELISpot detection board, the IL-4 capture antibody, the AQP-4 polypeptide, the IL-4 detection antibody with biotin labeling, the avidin-alkaline phosphatase conjugate, the substrate liquid nitrogen blue tetrazolium and the 5-Br-4-C1-3 indole phosphoric acid.

The means of implementation of this invention is further detailed in conjunction with the following accompanying drawings and embodiments.

DETAILED DESCRIPTION OF THE PREFERRED EMBODIMENT

Figure 1:
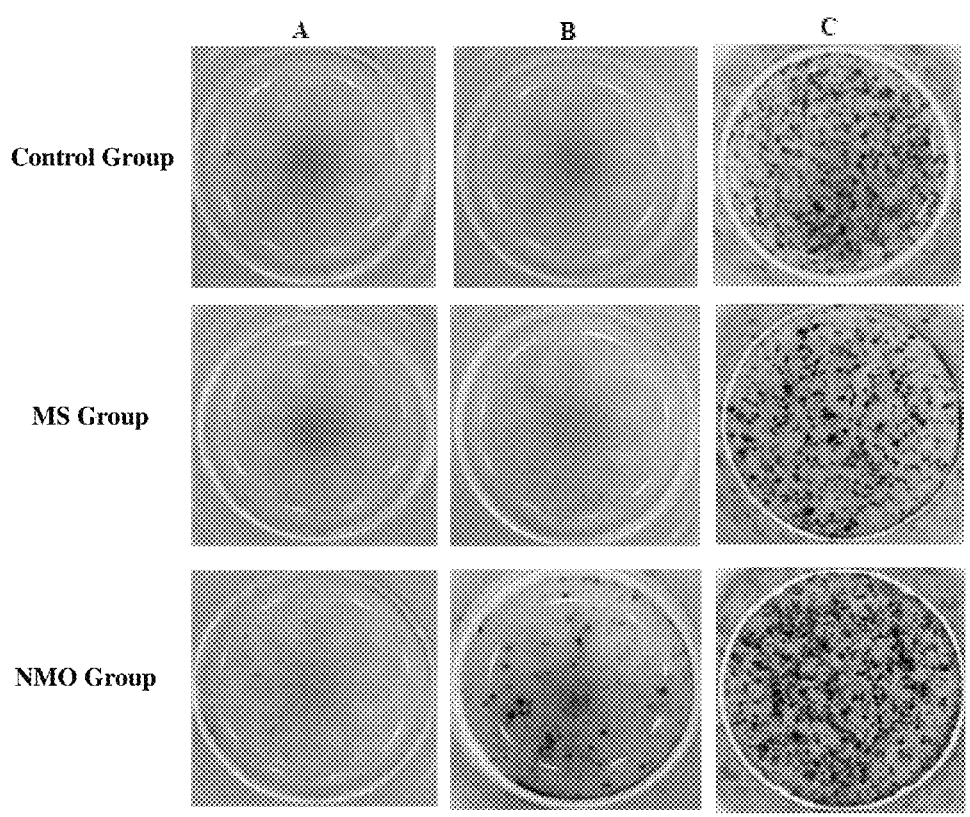
FIG. 1: This figure is the example of detection diagram of the embodiment. There are three groups in the embodiment, i.e. the control group of healthy people (the Control Group), the control group of multiple sclerosis (the MS group) and the NMO Group respectively. Among them, Row A is the negative control holes; Row B is the polypeptide holes and Row C is the positive control holes. This diagram shows that, it is totally possible to apply the polypeptide involved in this invention to diagnose and differentially diagnose the NMO disease in this embodiment.

This invention is applied to differentially diagnose 20 cases in the control group of healthy people (the Control Group), 20 cases in the control group suffering disease (multiple sclerosis victims, the MS Group) and 20 cases in the NMO group (the NMO Group), so as to preliminarily judge the specificity and sensitivity of this invention in the NMO diagnosis and then judge its clinical significance.

The detailed procedures are as follows:
(1): Coating:
Add 1:500 diluted IL-4 capture antibody into the ELISpot filtration membrane plate, at 100 ul/hole; after staying overnight at 4° C., use sterile phosphate buffered solution (PBS) to wash the plate for 3 times, at 3 min/time;
PBS containing 5% bovine serum albumin is added into each hold, incubated for 2 h at 37° C.; after sealing, it is stored at 4° C., for use within 1 week.

(2) Detection:

4-5 ml of victim or health person's peripheral anticoagulated blood for storage at the normal temperature, to be detected within 6 h;

Under the condition of aseptic processing, the 1640 culture medium is used to dilute the blood at a volume ratio of 1:1, evenly mixed and then added to the surface of lymphocyte separating medium of 1 time volume, forming an obvious interface; under the room temperature, 1000 g is centrifuged for 22 min;

Use the sterile suction tube to absorb the peripheral blood mononuclear cell (PBMC) of separating layer and place it in one sterile centrifugal tube; add 8 ml of 1640 culture medium without blood serum; taken 700 g for centrifuging for 7 min;

Abandon the supernatant culture medium, and add 6 ml of 1640 culture medium suspended cells containing 10% calf serum; taken 300 g for centrifuging for 5 min;

Abandon the supernatant, and then add 500 ul of 1640 culture medium containing 10% calf serum; take 10 ul cell suspension; after adding 40 ul trypan blue and mixing it evenly, take 10 ul on the blood counting chamber for counting under the microscope; use the 1640 complete medium to dilute the cell to $5 \times 10^6$ cells/ml;

Add the following reagents into the above coated ELISpot holes respectively: 50 ul of culture medium (negative control), 50 ul of 1:1000 CD3 antibody (positive control) and 50 ul of 50 ug/ml polypeptide (detection hole);

After adding 100 ul of cell suspension into each hole, put it into 5% CO2 incubator at 37° C. for cultivation for 20 hours;

Abandon the culture medium, and use 200 μl of PBS to wash for 5 times;

Add 100 μl of 1:300 diluted IL-4 detection antibody with biotin labeling into each hole; after incubating for 2 h under the room temperature, add 200 μl of PBS into each hole to wash for 5 times;

Add 100 μl of diluted 1:1000 avidin-alkaline phosphatase conjugate diluted with PBS into each hole; after reaction for 30 min under the room temperature, use the PBS to wash for 5 times, and each time lasts for 3 min;

Add 100 μl of substrate liquid nitrogen blue tetrazolium and 5-Br-4-Cl-3 indole phosphoric acid into each hole; place under the room temperature in a closed way for 15 min till spots appear; use the tap water to wash and then air-dry it; check the quantity of spots for statistics and analyses.

Result Judgment: If there are 0-5 spots in the negative holes and the spot numbers of detection holes minus the spot numbers of negative control holes are ≥6, it is judged as positive; if the spot numbers of negative control holes are ≥6 spots, it can be judged as positive only when the spot numbers of detection holes are ≥2 times of the spot numbers of negative control holes.

Figure 2:
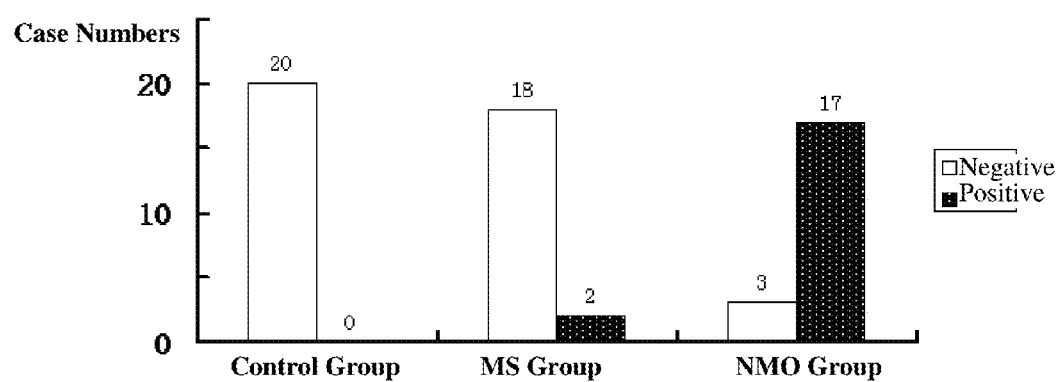
FIG. 2: This figure is a statistical diagram of detection results of the embodiment. This diagram shows that, 17 of 20 NMO victims are successfully detected with this patent, with a detectable rate of 85%.

(3) Result: According to the above judgments, all detection results can be judged as negative or positive ones (FIG. 1 and FIG. 2); it is preliminarily held that the specificity of NMO diagnosis by applying this invention is 95% and the sensitivity thereof is 85%.

It should also be understood that after reading the above-described contents relating to this invention, technicians in this field may make various changes or modifications to this invention, and these equivalent forms also fall in the range defined by the Claims attached to this application.

---

---

What is claimed is:

1. An isolated polypeptide having the amino acid sequence of -SEQ ID NO: 1 for diagnosing neuromyelitis optica.

2. A method for diagnosing neuromyelitis optica in a subject comprising (a) isolating lymphocytes from the blood tissue of the subject; (b) culturing the lymphocytes in the culture media containing the isolated polypeptide according claim 1; (c) detecting the presence of interleukin 4 in the culture media of the step (b); and (d) diagnosing neuromyelitis optica in the subject based on the presence of interleukin 4 in the culture media.

3. A kit for diagnosing neuromyelitis optica in a subject comprising an isolated polypeptide the amino acid sequence of -SEQ ID NO: 1and interleukin 4 detection reagents.

4. The kit according to claim 3, wherein the interleukin 4 detection reagents comprising an interleukin 4 capture antibody and an interleukin 4 detection antibody.

* * * * *